(12) United States Patent
Andrews (10) Patent No.: US 7,460,648 B2
(45) Date of Patent: Dec. 2, 2008

(54) MECHANICAL INTERFACE ASSEMBLY

(75) Inventor: Gregory C. Andrews, Draper, UT (US)

(73) Assignee: Varian Medical Systems, Inc., Palo Alto, CA (US)

( * ) Notice: Subject to any disclaimer, the term of this patent is extended or adjusted under 35 U.S.C. 154(b) by 0 days.

(21) Appl. No.: 11/744,140

(22) Filed: May 3, 2007

(65) Prior Publication Data

US 2008/0273668 A1    Nov. 6, 2008

(51) Int. Cl.
*H01J 35/08* (2006.01)
*H05G 1/00* (2006.01)

(52) U.S. Cl. ........................ 378/144; 378/210

(58) Field of Classification Search .......... 378/143, 378/144, 119, 210
See application file for complete search history.

(56) References Cited

U.S. PATENT DOCUMENTS

| | | | | |
|---|---|---|---|---|
| 4,736,400 A | * | 4/1988 | Koller et al. | 378/125 |
| 5,577,093 A | * | 11/1996 | Benz et al. | 378/125 |
| 5,930,332 A | * | 7/1999 | Eggleston et al. | 378/144 |
| 6,212,753 B1 | | 4/2001 | Derakhshan et al. | |
| 6,751,293 B1 | * | 6/2004 | Barrett | 378/144 |
| 6,819,742 B1 | * | 11/2004 | Miller | 378/144 |

* cited by examiner

*Primary Examiner*—Irakli Kiknadze
(74) *Attorney, Agent, or Firm*—Workman Nydegger (57) ABSTRACT

A mechanical interface assembly that includes an adjustable element having first and second states such that in the first state, the adjustable element is radially compliant, and in the second state, the adjustable element is substantially non-radially compliant. The adjustable element also includes a mating element configured to interface with a mating component. The mechanical interface assembly further includes an adjustment element configured to interface with the adjustable element such that a first position of the adjustment element corresponds to the first state of the adjustable element, and a second position of the adjustment element corresponds to the second state of the adjustable element.

20 Claims, 5 Drawing Sheets

MECHANICAL INTERFACE ASSEMBLY

BACKGROUND OF THE INVENTION

1. Field of the Invention

The present invention relates generally to x-ray systems, devices, and related components. More particularly, exemplary embodiments of the invention concern structures configured to aid in the management of relative motion between two or more attached components.

2. Related Technology

The ability to consistently develop high quality radiographic images is an important element in the usefulness and effectiveness of x-ray devices as diagnostic tools. However, various factors or conditions relating to the construction and/or operation of the x-ray device may operate to materially compromise the quality of radiographic images generated by the device. Likewise, such conditions can impair the operation of therapeutic x-ray devices. These conditions include, among others, vibration caused by moving parts of the x-ray device, and various thermally induced effects such as the occurrence of physical changes in the x-ray device components as a result of high operating temperatures and/or thermal gradients. While conditions such as these are diverse, it is frequently the case that the conditions are related to each other in some way, often to the extent that the occurrence of one condition is a direct consequence of the occurrence of one or more other conditions.

By way of example, vibration may occur as a consequence of thermally-induced relative movement between components of the x-ray device. In particular, as the various components and mechanical joints are subjected to repeated elastic deformation under the influence of the extreme thermal cycles typically experienced in connection with the operation of an x-ray device, the connections between the components can loosen and the components may become misaligned or separated. Thus, during operation of the x-ray device, such misalignment and/or separation of components is often manifested in the form of vibration and/or noise.

Typically, the occurrence of such vibration is most prevalent where components are joined together through the use of fasteners or similar arrangements. On the other hand, vibration problems, while still cause for concern, may occur relatively less commonly where components have been permanently attached to each other, such as by welding or brazing for example.

Further, yet other factors sometimes exist that can also cause and/or aggravate vibration in the x-ray device. For example, relative differences in the thermal expansion rates of connected components may cause the components to separate from each other over a number of thermal cycles. As discussed below, the existence of vibration due to the foregoing, and other, conditions presents problems with respect to the quality of the radiographic images produced by the x-ray device, or with respect to the operation of therapeutic devices.

In general, the generation of a radiographic image involves the use of a cathode, or other electron emitter, to direct a beam of electrons at an anode, or target, having a target surface composed of a material such that, when the target surface is struck by the electrons emitted by the cathode, x-rays are produced. In order to produce a high quality image or achieve some other desired result, the electrons of the electron beam are focused at a particular location, or focal spot, on the surface of the target.

In general, the quality of the radiographic images produced by the x-ray device depends largely on reliable and consistent positioning of the focal spot. Thus, any changes to the location and positioning of the focal spot, such as may occur as a result of vibrations or other conditions, during the generation of the radiographic image can materially impair the quality of the generated image and, thus, the effectiveness of the x-ray device. Operation of therapeutic devices likewise relies on maintenance of the focal spot location.

While any number of x-ray device components and assemblies may be adversely affected by vibration, the anode assembly, sometimes also referred to as the target assembly, is particularly susceptible to vibration related problems. This is due at least in part to the fact that at least some of the various components of anode assemblies are attached together with fasteners, rather than by processes such as welding or brazing.

In light of the foregoing concerns, various approaches have been taken with a view towards reducing the vibration that occurs as a result of relative movement between attached components of the x-ray device. In one approach, an interference fit, implemented either by thermal interference or pressing, is employed between the attached components. However, both of these approaches to interference fitting have proven problematic.

With respect to the interference press fit for example, significant forces must be exerted on the constituent portions of the assembly in order to join those portions together. Moreover, the resulting fit between the components of an assembly is often unsatisfactory because the runout between the components is unacceptably large. The runout may be the result of the presence of burrs or other assembly related conditions. A related concern is that such problems often cannot be readily resolved. For example, an assembly must sometimes be disassembled and reassembled a number of times until a proper fit between the components of the assembly is achieved. However, where a total indicated runout ("TIR") requirement for the assembly is relatively small, such as 0.001" or less for example, it may not be possible to disassemble and reassemble the components and still maintain compliance with the TIR requirements.

Thermal interference fit processes are also problematic. For example, typical thermal fit processes employed in connection with the attachment of a pair of components to each other require that one of the components be heated and the other component be cooled so that the component that has contracted as a result of the cooling process can be readily positioned within the component that has expanded as a result of the heating process. Because the temperature differential between the components must often be quite large for the assembly process to be effective, the handling of very cold and/or very hot components can be hazardous to the assembler. Moreover, the assembly process must be performed relatively quickly because the large temperature differential between the components exists only for a short period of time.

In yet another alternative approach, one of the components of an assembly is configured so as to allow for a measure of compliance in the radial direction. Such components thus obviate the need for the thermal processes necessitated by thermal interference fits. These compliant components also eliminate the need for exertion of large forces such as are typically employed in non-thermal interference fit processes. However, while these types of compliant components eliminate some problems, those components introduce new problems.

For example, the introduction of radial compliance means that the compliant component necessarily lacks radial stiffness. The lack of radial stiffness can be problematic inasmuch as components constructed in this fashion may permit more relative movement of an attached component in the radial direction than is desirable. Such movement may have various undesirable effects, including lowering a critical resonance point associated with a rotating assembly and/or permitting unacceptable levels of anode assembly motion at relatively high g-force levels.

Yet another approach to the resolution of problems such as those noted above involves the use of parts configured such that an intentional radial clearance is defined between the parts. At least one concern with this approach is readily apparent. Particularly, the radial clearance between the parts permits movement of each part relative to the other.

Another concern with approaches involving the intentional introduction of radial clearances between joined parts relates to the respective thermal expansion coefficients of those parts. That is, exposure of the assembled parts to thermal gradients such as are commonly experienced in x-ray device operating environments can result in relative motion between the parts as one part expands more quickly than the other. In one particular example, the component with the relatively higher coefficient of thermal expansion may, during operation of the device in which the assembly is employed, contact a radial surface of the component with the relatively lower coefficient of thermal expansion. After this contact is made, the addition of more heat to the assembly may cause the faster expanding component to push off the radial surface of the more slowly expanding component, thus resulting in unwanted relative movement between the attached components.

In view of the foregoing, and other, problems in the art, it would be useful to provide structures configured to aid in the management of relative motion between two or more attached components.

BRIEF SUMMARY OF AN EXAMPLE EMBODIMENT OF THE INVENTION

In general, embodiments of the invention are concerned with structures configured to aid in the management of relative motion between two or more components that are attached together.

In one example embodiment, a mechanical interface assembly is provided that includes an adjustable element having first and second states such that in the first state, the adjustable element is radially compliant, and in the second state, the adjustable element is substantially non-radially compliant. The adjustable element also includes a mating element configured to interface with a mating component. The mechanical interface assembly further includes an adjustment element configured to interface with the adjustable element such that a first position of the adjustment element corresponds to the first state of the adjustable element, and a second position of the adjustment element corresponds to the second state of the adjustable element.

In operation, the mating element of the adjustable element is brought into engagement with the mating component. Once the mating element is positioned in this fashion, the adjustable element is then manipulated until the radial compliance of the adjustable element has been substantially eliminated. In one embodiment, substantial elimination of this radial compliance results in an arrangement where the adjustable element has been deformed to an extent that the adjustable element and the mating component are in contact with each other.

Thus disposed, the adjustable element and the mating component are substantially incapable of any significant radial movement, relative to each other. The adjustable element and the mating component can then be secured together in an axial direction with fasteners.

BRIEF DESCRIPTION OF THE DRAWINGS

In order that the manner in which the above-recited and other aspects of the invention are obtained, a more particular description of the invention will be rendered by reference to specific embodiments thereof which are disclosed in the appended drawings. Understanding that these drawings disclose only typical embodiments of the invention and are not therefore to be considered limiting of its scope, the invention will be described and explained with additional specificity and detail through the use of the accompanying drawings in which.

DETAILED DESCRIPTION OF SOME EXAMPLE EMBODIMENTS OF THE INVENTION

Reference will now be made to the drawings to describe various aspects of example embodiments of the invention. It should be understood that the drawings are diagrammatic and schematic representations of such exemplary embodiments and, accordingly, are not limiting of the scope of the present invention, nor are the drawings necessarily drawn to scale.

I. Some Structural Aspects of an Example Device

Figure 1A:
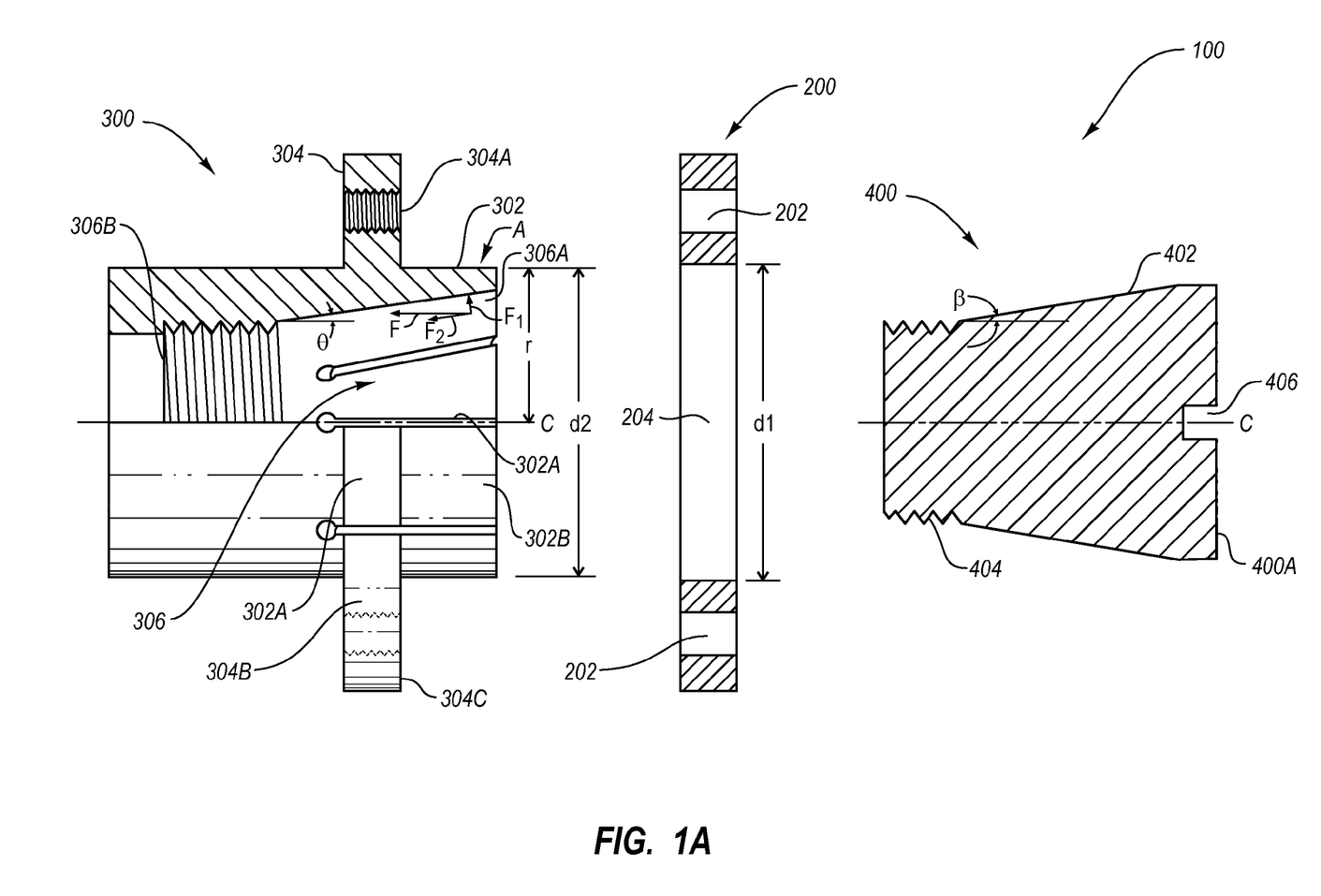
FIG. 1A is an exploded view of an example embodiment of the invention.
Figure 1B:
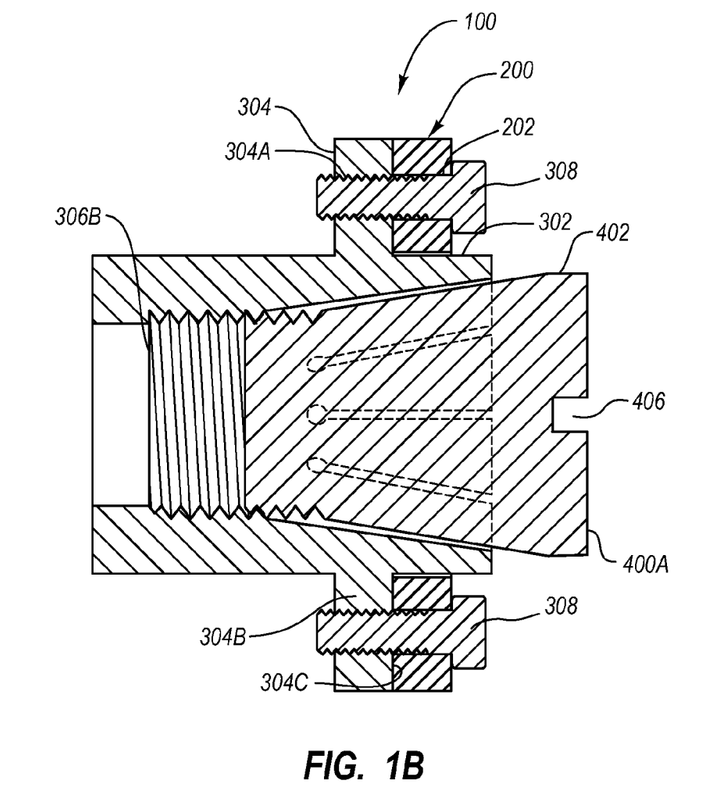
FIG. 1B is a side view of an assembled device and discloses aspects of the interface of the assembled device with a mating component.
Figure 1C:
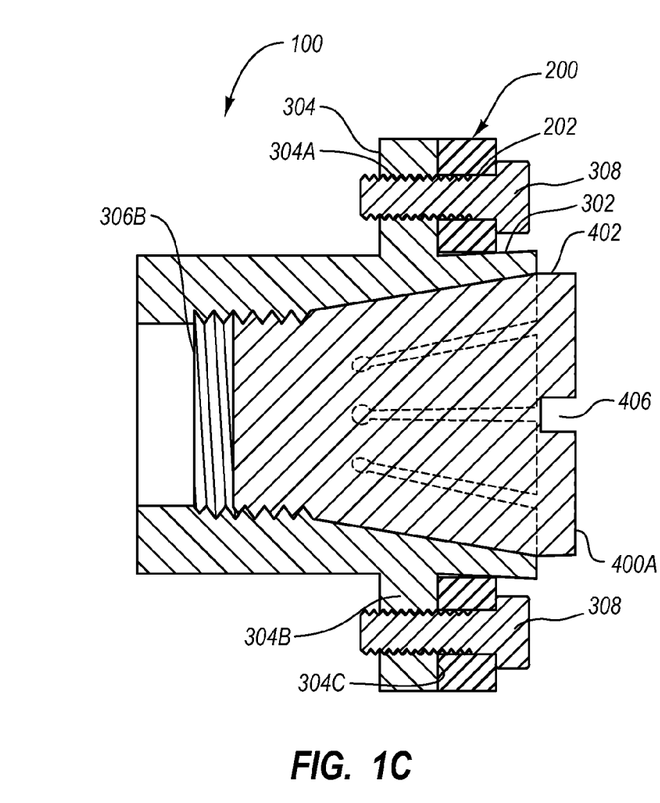
FIG. 1C is a side view of an assembled device and discloses a body of the device when in a deformed state such that radial movement of attached components is substantially precluded.

With general reference now to FIGS. 1A-1C, details are provided concerning one example embodiment of the invention. In the example of FIGS. 1A-1C, a mechanical interface assembly is denoted generally at 100. The mechanical interface assembly 100 is configured to interface with a mating component 200.

In general, the mechanical interface assembly 100 may be configured in any form necessary to facilitate attachment and securement of the mechanical interface assembly 100 to the mating component 200. Thus, the specific configuration of the mechanical interface assembly 100 in FIGS. 1A-1C represents but one example embodiment. Moreover, the mechanical interface assembly 100 may be incorporated into another component that is desired to be attached to the mating component 200.

The components of the mechanical interface assembly 100 may be constructed of any suitable material(s) including metals such as, but not limited to, steel, copper alloys, or any other materials suitable for the intended application. Moreover, the mechanical interface assembly 100 may be forged, cast, milled, or formed in any other fashion suitable for the intended application. In at least some embodiments, the components of the mechanical interface assembly 100, which may include both an adjustable element and an adjustment element, have substantially the same coefficient of thermal expansion. In yet other embodiments, the mechanical interface assembly 100 may comprise several components, two or more of which may have different coefficients of thermal expansion.

As to the example mating component 200, the scope of the invention is not limited to use of the mechanical interface assembly 100 in connection with any particular mating component 200. Rather, embodiments of the invention may be configured to be employed in connection with any of a variety of different mating components.

Thus, in one example embodiment, the mechanical interface assembly 100 is incorporated into a bearing hub of an x-ray device rotating anode assembly. In this example, the mating component 200 is implemented as a flange that comprises an element of another component (not shown) to which the bearing hub is attached. In the illustrated embodiment, the mating component 200 includes a plurality of thru holes 202, each of which is configured to receive a corresponding fastener (not shown) so that the mating component 200 can be removably attached to the adjustable element 300. The example mating component 200 further defines a central opening 204 having a diameter "$d_1$." In general, the central opening 204 is configured and arranged to receive a portion of the adjustable element 300, as disclosed in further detail below.

With continued reference now to the example embodiment disclosed in FIGS. 1A-1C, the mechanical interface assembly 100 includes an adjustable element 300 that is configured to interface with an adjustment element 400. In the example embodiment disclosed in FIGS. 1A-1C, the adjustable element 300 is implemented as a collet, and the adjustment element 400 is implemented as a collet expander.

As indicated in FIGS. 1A-1C, the adjustable element 300 includes a body 302 to which a mating element 304 is attached. The body 302 and mating element 304 may be integrally constructed with each other, or may comprise discrete elements that have been attached together. In general, the body 302 is configured so as to be capable of assuming various different states. More specifically, and as discussed in further detail below in connection with the adjustment element 400, a radius "r" associated with the body 302 may be varied such that different radii of the body 302 correspond to different respective states. Thus, components possessing the aforementioned characteristic of body 302 may be referred to herein as being radially compliant.

In the example embodiment of FIGS. 1A-1C, the radial compliance of the body 302 is achieved through the use of one or more cutouts 302A. In the example illustrated embodiment, a group of cutouts 302A are defined by the body 302 at various locations. In this example embodiment, the cutouts 302A have a generally key-shaped configuration. However, other cutout configurations may alternatively be employed.

More generally, the size, number, geometry and orientation of the cutout(s) employed in a particular embodiment may be varied as necessary to suit a particular application. For example, two diametrically opposed cutouts may be adequate for some applications, while other applications may require a different arrangement of more than two cutouts. As another example, the cutouts need not be axially oriented but some or all of the cutouts could instead be oriented off-axis, that is, non-parallel with respect to axis "C." Thus, the scope of the invention is not limited to the example configuration and arrangement of cutouts disclosed in the Figures. It should be noted as well that the term cutout is not intended to imply that the cutouts are formed or created by a particular production process(es).

Among other things, the presence of the cutouts 302A enables a portion of the body 302 to be deformed. That is, the fingers 302B that are spaced apart by the cutouts 302A can be compressed together or pushed apart as desired. Consequently, the value of the radius "r" of the body 302 can be correspondingly adjusted. Specifically, the radius "r" can be decreased by compressing the fingers 302B together, or the radius "r" can be increased by pushing the fingers 302B apart. As disclosed below, the radial compliance of the body 302 has various useful implications.

With continued reference to the example embodiment of FIGS. 1A-1C, the body 302 of the adjustable element 300 has an undeformed outside diameter "$d_2$" that is smaller than the inside diameter "$d_1$" of the central opening 204 defined by the mating part 200. As a result, end "A" of the body 302 can be received within the mating part 200 prior to adjustment of the radius "r" of the body 302. More generally, however, embodiments of the invention can be configured in any fashion necessary to enable attachment of the mechanical interface assembly to a mating component.

With continued attention to the adjustable element 300, the mating element 304 is generally configured and arranged to facilitate attachment of the adjustable element 300 to another component, such as the mating component 200 for example. In the example of FIGS. 1A-1C, the mating element 304 is implemented as a flange that defines a group of threaded holes 304A. In general, the number and arrangement of the threaded holes 304A correspond to the number and arrangement of the thru holes 202 defined by the mating component 200. Thus, the adjustable element 300 can be removably secured to the mating component 200 with bolts or other suitable threaded fasteners.

In one alternative arrangement, the holes defined by the mating component 200 are threaded, and the holes defined by the mating element 304 are implemented as thru holes. In yet another alternative arrangement, all of the holes in the mating component 200 and the mating element 300 are thru holes. However, the scope of the invention is not limited to the foregoing, or any other, particular configuration(s).

With continued reference to the mating element 304, FIGS. 1A-1C indicate that the cutouts 302A extend axially through the mating element 304. Thus, the segments 304B that are defined by the cutouts 302A are each attached to a corresponding finger 302B of the body 302, as best shown in FIG. 1A. Consequently, displacement of a finger 302B results in a corresponding displacement of the associated segment 304B.

The mating element 304 further defines a seating surface 304C. As best indicated in FIGS. 1B and 1C, the seating surface 304C is configured and arranged to contact mating part 200 when mating part 200 has received the body 302 of the mechanical interface assembly 100.

As noted earlier herein, the example embodiment of the adjustable element 300 is configured to operate in conjunction with a corresponding adjustment element 400. To that end, the adjustable element 300 defines a cavity 306 that includes a tapered portion 306A and defines a taper angle θ, and the cavity 306 further includes a threaded portion 306B.

Correspondingly, the adjustment element 400, which may be implemented in a hollow form, or a substantially solid form, includes a tapered portion 402 that defines a taper angle β, and the adjustment element 400 further includes a threaded portion 404. In at least some embodiments, the adjustment element 400 is substantially non-radially compliant.

The taper angle β of the tapered portion 402 may or may not be the same as the taper angle θ defined by the tapered portion 306A of the adjustable element 300. Additionally, and as best shown in FIGS. 1B and 1C, the external threads of the threaded portion 404 of the adjustment element 400 are configured and arranged to engage the internal threads of the threaded portion 306B of the adjustable element 300.

The illustrated example of the adjustment element 400 further includes an engagement feature 406, implemented in this example as a pair of notches disposed at a terminal end 400A of the adjustment element 400. In this example, the engagement feature 406 is configured to interface with a tool, such as a spanner for example, so that the tool can be used to rotate the adjustment element 400 into a desired position relative to the adjustable element 300. Various other engagement features and/or tools may alternatively be employed however, and the scope of the invention is not limited to the aforementioned example embodiment.

With continued reference to the adjustment element 400, various structural modifications can be implemented in order to achieve a desired effect with respect to the radial stiffness of the mechanical interface assembly 100 and the mating component 200. For example, parameters such as, but not limited to, the engagement length, that is, the length of the threaded portion of the adjustment element, and the wall thickness of the adjustment element can be selected to facilitate achievement of a particular desired radial stiffness. As another example, the taper angle β of the adjustment element may also be selected so that a desired effect can be achieved.

II. Some Operational Aspects of an Example Device

Directing particular attention now to FIGS. 1B and 1C, details are provided concerning various operational and other aspects of the example mechanical interface assembly 100. As noted earlier herein, the mechanical interface assembly 100 may be implemented as an element of a component that is desired to be attached to the mating component 200. As well, the mating component 200 may comprise an element of a component to which it is desired to attach the component that includes the mechanical interface assembly 100.

As best indicated in FIGS. 1B and 1C, the mechanical interface assembly 100 is received within the mating part 200 such that end "A" of the mechanical interface assembly 100 extends into, or completely through in some cases, the central opening 204 defined by the mating part 200. Thus arranged, the mating part 200 resides on the seating surface 304C defined by the mating element 304 of the mechanical interface assembly 100. At this stage, one or more of the fingers 302B may or may not be in contact with the sides of the mating part 200 that define the central opening 204.

When the mating part 200 and the mechanical interface assembly 100 have been positioned as just described, the adjustment element 400 can then be positioned in the cavity 306 defined by the body 302 of the adjustable element 300. In embodiments where the maximum outside diameter of the adjustment element 400 does not exceed "$d_1$" the adjustment element 400 can be positioned in the cavity 306 defined by the body 302 prior to placement of the mating part 200 on the seating surface 304C.

After the mating part 200 has been positioned on the seating surface 304C, and the adjustment element 400 positioned in the cavity 306, the threaded portion 404 of the adjustment element 400 can then be brought into engagement with the threaded portion 306B of the adjustable element 300. Rotation of the adjustment element 400 further engages the threaded portion 404 with the threaded portion 306B. As the adjustment element 400 is rotated, the adjustment element 400 advances further into the cavity 306. Correspondingly, the terminal end 400A advances along the tapered portion 306A of the cavity 306.

Because the tapered portion 306A becomes progressively narrower towards the threaded portion 306B, the advancement of the terminal end 400A results in the exertion of a force "F" by the adjustment element 400 on the adjustable element 300. As indicated in the simplified force diagram associated with FIG. 1A, a first component "$F_1$" of the force "F" exerted by the adjustment element 400 acts substantially normally with respect to the surface of the tapered portion 306A, while a second component "$F_2$" of the force "F" acts substantially parallel to the surface of the tapered portion 306A.

Because both the terminal end 400A and the tapered portion 306A of the cavity 306 are substantially circular in this example embodiment, the force "F" is exerted substantially uniformly about an axis "C" associated with the mechanical interface assembly 100. Accordingly, and as best shown in FIG. 1B, as the terminal end 400A advances downward along the tapered portion 306A toward the threaded portion 306B, exertion of the force "F" causes the fingers 302B to move apart from each other and into contact with the mating part 200.

The force "F" that is exerted by the adjustment element 400 on the fingers 302B and, thus, on the mating part 200, can be increased by continued advancement of the adjustment element 400 into the cavity 306. At such time as the force "F" exerted on the mating part 200 achieves a desired magnitude, the mechanical interface assembly 100 can then be secured to the mating part 200 in the axial direction with suitable fasteners 308. In this way, relative movement between the mechanical interface assembly 100 and the mating part 200 along axis "C" is substantially precluded.

Moreover, and as suggested above, radial movement of the mechanical interface assembly 100 and the mating part 200 relative to each other is substantially precluded as well. In particular, expansion of the body 302 within the central opening 204 of the mating component 200, manifested as a relative increase in the diameter "$d_2$," is effected by virtue of the force "F" exerted by the actuating part 400 and transmitted to the mating party 200 by the fingers 302B. Thus, although the extent to which the body 302 can be axially expanded is limited by the dimensions of the central opening 204, the exertion and maintenance of the force "F" beyond the magnitude required to merely achieve contact between the body 302 and the mating component 200 results in an arrangement where relative radial motion between the mechanical interface assembly 100 and the mating part 200 is substantially precluded.

Thus, when the actuating part 400 is not engaged with the threaded portion 306B of the cavity 306, the body 302 is in a radially compliant state. Further, the body 302 remains in the radially compliant state until the actuating part 400 has moved to a position where all of the fingers 302B are in contact with the mating component 200.

As the foregoing makes clear then, a first position of the actuating part 400 corresponds with a radially compliant state of the body 302, while a second position of the actuating part 400 corresponds with a substantially non-radially compliant state of the body 302. That is, in the non-radially compliant state, the force exerted by the fingers 302B on the mating component 200 may be increased, but no substantial change occurs to the radius "r" of the body 302 once contact between the fingers 302B and the mating component 200 is achieved.

Among other things then, embodiments of the invention are effective in substantially precluding relative axial and radial movement between a pair of components that are attached to each other. As disclosed elsewhere herein, this functionality is useful in a variety of environments, one example of which concerns x-ray devices. Additionally, embodiments of the invention enable ready assembly and disassembly of the mating components, and also enable radial contact on respective perpendicular feature planes of the mechanical interface assembly and the mating component.

As noted earlier herein, the radial stability achieved in connection with example embodiments of the invention may prove useful in any of a number of different applications. In one example application, where the mechanical interface assembly is implemented in connection with a bearing assembly for a rotating anode, the radial stability provided by the mechanical interface assembly may facilitate enhanced control of the focal spot location by providing for a relative decrease in vibrations that would otherwise arise due to relative radial movement between attached components. Such enhanced focal spot control may correspond to improved radiographic or other images.

III. An Example Operating Environment and Associated Example Embodiment a. Operating Environment With reference now to FIG. 2, details are provided concerning an example of an operating environment, specifically, an x-ray device 500, in connection with which at least one example embodiment of the invention may be employed. It should be noted here that x-ray devices contemplated as being within the scope of the invention include, but are not limited to, both therapeutic and diagnostic devices.

It should also be noted that while various aspects of some example embodiments of the invention are disclosed herein in the context of x-ray devices and related components, the scope of the invention is not so limited. That is, some or all of the aspects of the disclosure hereof may be employed in connection with various other operating environments and devices as well.

Accordingly, the scope of the invention should not be construed to be limited solely to x-ray systems, devices, and components. Rather, the scope of the invention extends, at least, to devices and applications where it may be desirable to limit and/or prevent relative radial and/or axial movement between components that are attached together.

Figure 2:
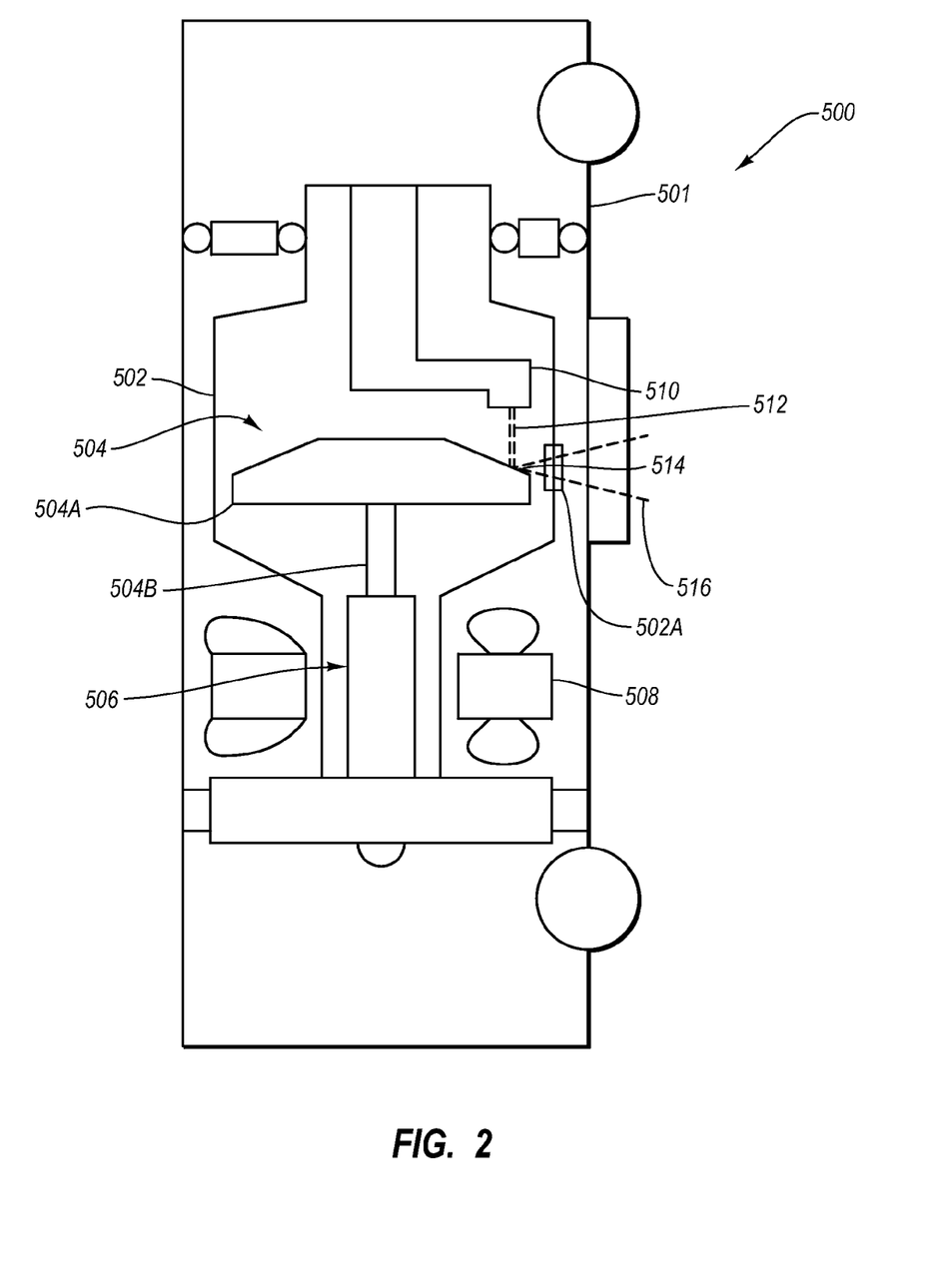
FIG. 2 is a top view of an x-ray tube operating environment in which some embodiments of the invention may be employed.

Turning now to FIG. 2, the x-ray device 500 includes a housing 501 within which a vacuum enclosure 502 is disposed. The housing 501 may or may not include fluid connections (not shown) configured and arranged so that a flow of coolant can be directed into one of the fluid connections, circulated within the housing 501 so as to cool components disposed within the housing 501, and then returned to an external cooling system (not shown) by way of the other cooling connection.

The vacuum enclosure 502 further includes an x-ray transparent window 502A comprised of beryllium or other suitable material(s). An anode assembly 504 is disposed within the vacuum enclosure 502 and includes an anode 504A having a target surface comprised of tungsten or other suitable material(s). The anode 504A is mounted to a shaft 504B that is rotatably support by a bearing assembly 506. In one example embodiment, the shaft 504B is connected, either directly or indirectly, to another shaft (not shown) positioned within a housing (not shown) of the bearing assembly 506.

A stator assembly 508 imparts a high speed rotational motion to the shaft 504B and, thus, to the anode 504A. Also disposed within the vacuum enclosure 502 is a cathode assembly 510 that is positioned to direct a stream of electrons at the target surface of the anode 504A. The x-ray device 500 further includes a pair of high voltage connections (not shown) configured and arranged so that a high voltage potential can be established between the cathode assembly 510 and the anode 504A.

In operation, energy is supplied to the cathode assembly 501, thereby stimulating the emission of a stream of electrons 512. The high voltage potential between the cathode assembly 501 and the anode 504A causes the emitted electrons to accelerate rapidly toward a focal spot 514 on the rotating target surface of the anode 504A. As the electrons 512 strike the target surface, x-rays 516 are generated and exit the vacuum enclosure 502 through the window 502A.

As noted elsewhere herein, the generation of high quality radiographic images, or performance of other processes in diagnostic devices, requires a stable focal spot. To that end, one example embodiment of the invention is concerned with a bearing assembly that includes a mechanical interface assembly such as is disclosed herein. The bearing assembly can be employed in an x-ray device, but the bearing assembly and variations thereof may find use in other applications as well.

b. Example Embodiment for X-Ray Device Environment

Figure 3:
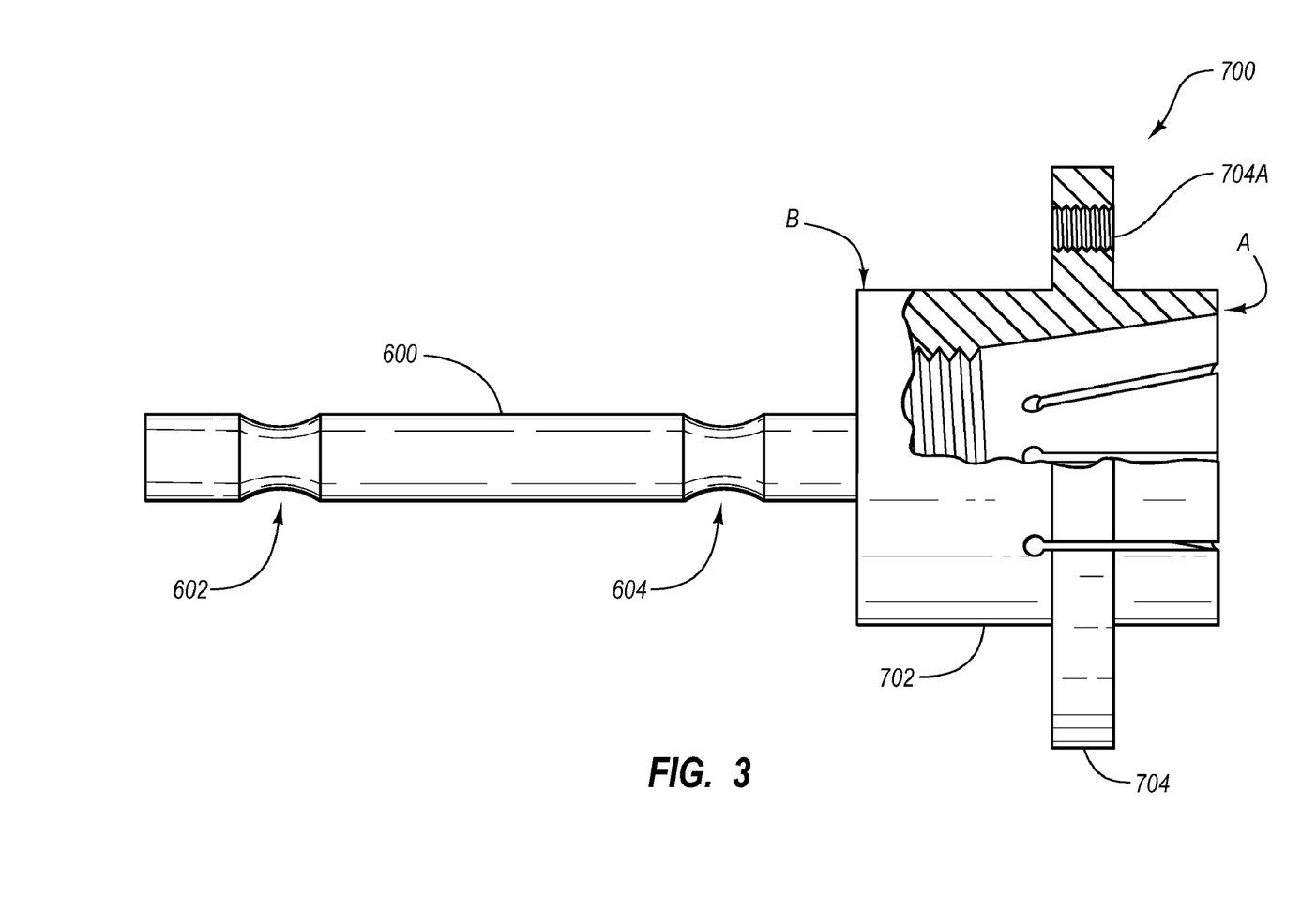
FIG. 3 is a side view of an x-ray device component incorporating a mechanical interface assembly.

Turning now to FIG. 3, details are provided concerning a shaft, such as may be employed in a bearing assembly, that is implemented in connection with a mechanical interface assembly. The bearing assembly can be employed in a variety of environments, including x-ray devices. In one example implementation, the bearing assembly rotatably supports another shaft to which an anode of an x-ray device is at least indirectly mounted.

In the embodiment disclosed in FIG. 3, the mechanical interface assembly 700 includes a body 702 having ends "A" and "B" similar to the ends "A" and "B" of the body 302 indicated in FIGS. 1A-1C. As indicated in FIG. 3, the shaft 600 is welded or otherwise attached to end "B." The body 702 may be similar, or identical, to the body 302 disclosed in FIGS. 1A-1C. In one example embodiment, the body 702 may define an opening within which the shaft 600 is received. In an alternative embodiment, no opening is defined in the body 702 for receiving the shaft 600 and the shaft 600 is, instead, attached to the underside of the body 702 at end "B."

As indicated in FIG. 3, the shaft 600, which may comprise an element of a bearing assembly, defines a pair of races 602 and 604 that cooperate with corresponding races of a pair of bearing rings (not shown) to confine respective sets of bearing balls (not shown). In this way, the shaft 600 is rotatably supported by the bearings.

Turning now to the mechanical interface assembly 700, the end "A" of body 702 can be configured to be received within, and thus interface with, any of a variety of mating components. Correspondingly, mating element 704 can be configured and arranged to interface with such mating components. In one example, the mating element 704 defines a plurality of threaded holes 704A that are each sized and arranged to align with corresponding holes of a mating component.

As noted above, embodiments of the mechanical interface assembly 700 may be configured to interface with a variety of mating components. Examples of such mating components include, but are not limited to, rotor covers, and anodes.

Moreover, embodiments of the mechanical interface assembly 700 may comprise an element of, or be implemented as, any of a variety of components. By way of example, a mechanical interface assembly may be implemented as a bearing hub such as would be employed in a rotating anode x-ray device. However, the scope of the invention is not limited to this example embodiment and, instead, broadly extends to any other component in which a mechanical interface assembly such as is disclosed herein is employed.

IV. Another Example Embodiment

Figure 4:
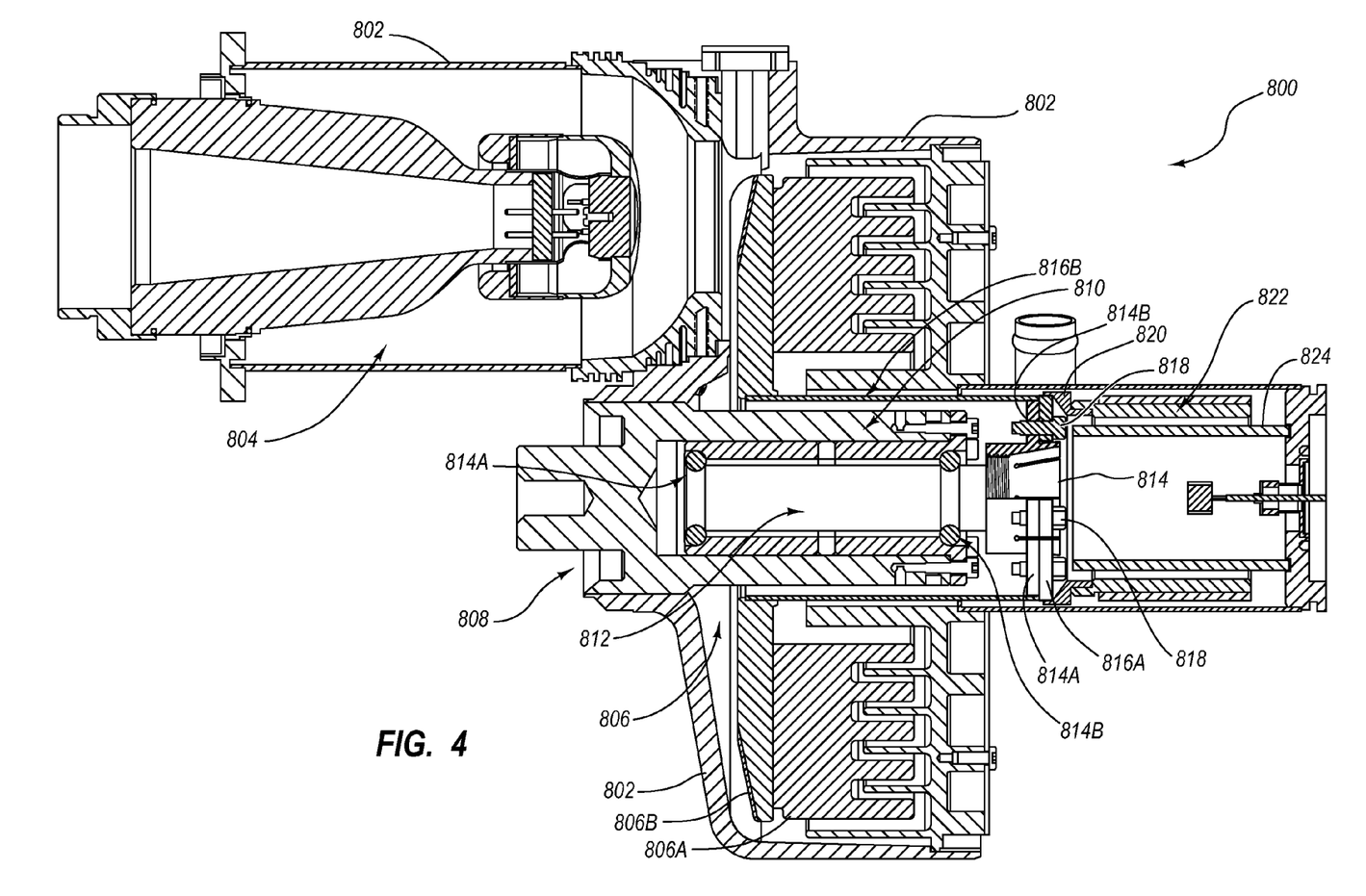
FIG. 4 is a cross-sectional view of an x-ray device that includes a mechanical interface assembly configured and arranged to interconnect a rotor shaft and a rotor cylinder stem.

With reference now to FIG. 4, details are provided concerning an x-ray device 800 that employs a mechanical interface assembly. In this example embodiment, the x-ray device 800 includes a vacuum enclosure 802 within which a cathode assembly 804 and rotating anode assembly 806 are disposed. The rotating anode assembly 806 includes an anode 806A having a target surface 806B positioned to receive electrons emitted by the cathode assembly 804. In general, the anode 806A is rotatably supported by a bearing assembly 808 that includes a bearing housing 810 within which a shaft 812 is positioned. The shaft 812 is rotatably supported by a pair of bearings 814A and 814B that are positioned within the bearing housing 810.

Inasmuch as the shaft 812 is similar in many aspects to the example shaft 600 disclosed in FIG. 3, the discussion of the example embodiment of FIG. 4 will place emphasis primarily on the implementation of the shaft 812 within the x-ray device 800.

With more particular reference now to the shaft 812, a mechanical interface assembly 814 is included that is attached at one end of the shaft 812. The mechanical interface assembly 814 and the shaft 812 may be integral with each other, or may comprise separate elements that have been joined together. A rotor cylinder assembly 816, to which the anode 806A is attached, is mounted to a mating component 814A of the mechanical interface assembly 814. In this example configuration, the rotor cylinder assembly 816 includes a plate 816A to which a rotor cylinder 816B is attached. The plate 816A and rotor cylinder 816B may be integral with each other, or may comprise separate elements that have been joined together. As further indicated in FIG. 4, a transition piece 820 connects the rotor cylinder assembly 816 to the rotor 822. In some embodiments, the transition piece 820 may be welded or brazed to the rotor cylinder assembly 816 and/or to the rotor 822. The rotor 822 is positioned about a stator 824 that, when energized, imparts a rotary motion to the rotor 822.

With continued reference to the example embodiment of FIG. 4, the rotor cylinder assembly 816 and the shaft 812 can be radially secured, relative to each other, through operation of the mechanical interface assembly 814 in the manner disclosed elsewhere herein. In addition, the rotor cylinder assembly 816 and the mechanical interface assembly 814 of shaft 812 can be axially secured, relative to each other, through the use of fasteners 818. To this end, the rotor cylinder assembly 816 may define thru holes, each of which corresponds to a threaded hole 814B defined in the mating component 814A of the mechanical interface assembly 814.

As should be apparent from the foregoing discussion, employment of the mechanical interface assembly 814 in the shaft 812 of the example x-ray device 800 environment disclosed in FIG. 4 enables the rotor cylinder assembly 816 and, correspondingly, the anode 806A, to be both radially and axially secured with respect to the shaft 812. Moreover, because the rotor 822 is attached to the rotor cylinder assembly 816 by way of the transition piece 820, employment of the mechanical interface assembly 814 also enables the rotor 822 to be radially and axially secured with respect to the rotor cylinder assembly 816 and the anode 806A.

The disclosed embodiments are to be considered in all respects only as exemplary and not restrictive. The scope of the invention is, therefore, indicated by the appended claims rather than by the foregoing description. All changes which come within the meaning and range of equivalency of the claims are to be embraced within their scope.

What is claimed is:

1. An x-ray device, comprising:
    an x-ray device component; and
    a mechanical interface assembly, comprising:
        an adjustable element having first and second states such that in the first state, the adjustable element is radially compliant, and in the second state, the adjustable element is substantially non-radially compliant, and the adjustable element including a mating element configured to interface with the x-ray device component; and
        an adjustment element configured to interface with the adjustable element such that a first position of the adjustment element corresponds to the first state of the adjustable element, and a second position of the adjustment element corresponds to the second state of the adjustable element.

2. The x-ray device as recited in claim 1, wherein the adjustable element defines a tapered cavity configured to at least partially receive the adjustment element.

3. The x-ray device as recited in claim 1, wherein the adjustable element includes a set of threads configured and arranged to engage a corresponding set of threads of the adjustment element.

4. The x-ray device as recited in claim 1, wherein the adjustable element includes a plurality of cutouts that cooperatively define a plurality of radially compliant elements.

5. The x-ray device as recited in claim 4, wherein one of the cutouts is oriented in a substantially axial manner with respect to the adjustable element.

6. The x-ray device as recited in claim 1, wherein when the adjustable element is in the second state, a portion of the adjustable element is deformed relative to a configuration of the portion when the adjustable element is in the first state.

7. The x-ray device as recited in claim 1, wherein when the adjustment element is engaged with the adjustable element, rotation of the adjustment element corresponds with a change in position of the adjustment element relative to the adjustable element.

8. The x-ray device as recited in claim 1, wherein the adjustable element and the adjustment element each define an associated taper angle.

9. The x-ray device as recited in claim 1, wherein the adjustable element and the adjustment element each have substantially the same coefficient of thermal expansion.

10. The x-ray device as recited in claim 1, wherein the mating element comprises a flange.

11. The x-ray device as recited in claim 1, wherein when the adjustable element is in the second state, a change in a position of the adjustment element relative to the adjustable element corresponds to a change in a magnitude of a force exerted by the adjustable element.

12. The x-ray device as recited in claim 1, wherein the adjustment element is configured to both rotate and translate relative to the adjustable element when the adjustment element is engaged with the adjustable element.

13. An x-ray device, comprising:
    an x-ray device component;
    a radially compliant collet having a plurality of fingers arranged such that each finger is separated from a succeeding finger by a cutout, the fingers cooperatively defining a portion of a tapered cavity, the tapered cavity including a threaded portion, and the radially compliant collet including a mating element configured to interface with the x-ray device component; and a tapered collet expander having threads configured to engage the threaded portion of the tapered cavity of the radially compliant collet, the fingers being responsive to the position of the collet expander in the tapered cavity such that when the collet expander is in a first position, the fingers are in a radially compliant state, and when the collet expander is in a second position, the fingers are in a substantially non-radially compliant state.

14. The x-ray device as recited in claim 13, wherein the collet and collet expander each have substantially the same coefficient of thermal expansion.

15. The x-ray device as recited in claim 13, wherein the collet expander is substantially non-radially compliant.

16. A rotating anode assembly, comprising:

a rotor cylinder assembly;

a shaft including a mechanical interface assembly that is configured to be removably attached to the rotor cylinder assembly, and the mechanical interface assembly having first and second associated states such that in the first state, the mechanical interface assembly is radially compliant, and in the second state, the mechanical interface assembly is substantially non-radially compliant; and an adjustment element configured to interface with the mechanical interface assembly such that a first position of the adjustment element corresponds to the first state of the mechanical interface assembly, and a second position of the adjustment element corresponds to the second state of the mechanical interface assembly.

17. A rotating anode assembly as recited in claim 16, wherein a substantially radial force is exerted by the mechanical interface assembly on the rotor cylinder assembly when the mechanical interface assembly is both attached to the rotor cylinder assembly and is in the second state, a magnitude of the substantially radial force being adjustable by manipulation of the adjustment element.

18. A rotating anode assembly as recited in claim 16, further comprising an anode attached at least indirectly to the rotor cylinder assembly.

19. An x-ray device that includes the rotating anode assembly as recited in claim 16.

20. A rotating anode assembly as recited in claim 16, wherein the rotor cylinder assembly further comprises a rotor attached at least indirectly to the mechanical interface assembly.

* * * * *

UNITED STATES PATENT AND TRADEMARK OFFICE
CERTIFICATE OF CORRECTION

PATENT NO. : 7,460,648 B2 Page 1 of 1
APPLICATION NO. : 11/744140
DATED : December 2, 2008
INVENTOR(S) : Andrews It is certified that error appears in the above-identified patent and that said Letters Patent is hereby corrected as shown below:

Column 6
Line 37, change "300" to --304--

Column 8
Line 39, change "party" to --part--

Column 9
Line 58, change "support" to --supported--

Column 10
Lines 5 and 7, change "501" to --510--

Signed and Sealed this

Sixth Day of July, 2010

David J. Kappos
*Director of the United States Patent and Trademark Office*